United States Patent [19]

Prengel et al.

[11] Patent Number: 5,407,746
[45] Date of Patent: Apr. 18, 1995

[54] PLATELET-LIKE SUBSTRATES

[75] Inventors: Constanze Prengel, Weiterstadt; Johann Dietz, Dietzen bach; Angelika Thurn-Müller, Frankenthanl, all of Germany

[73] Assignee: Merck Patent Gesellschaft Mit Beshränkter Haftung, Darmstadt, Germany

[21] Appl. No.: 127,532

[22] Filed: Sep. 28, 1993

Related U.S. Application Data

[63] Continuation of Ser. No. 547,277, Jul. 3, 1990, abandoned.

[30] Foreign Application Priority Data

Jul. 6, 1989 [DE] Germany ............... 39 22 178.4

[51] Int. Cl.$^6$ .................................. B32B 5/16
[52] U.S. Cl. ........................... 428/403; 428/404; 428/406; 428/363; 424/63; 424/69; 106/415; 106/418; 106/467; 106/469; 106/436; 106/450; 106/DIG. 3
[58] Field of Search ............. 428/403, 404, 363, 406; 424/63, 69; 106/415, 418, 467, 469, DIG. 3, 436, 450

[56] References Cited

U.S. PATENT DOCUMENTS

| | | | |
|---|---|---|---|
| 3,331,699 | 7/1967 | Marshall et al. | 106/415 |
| 3,634,119 | 1/1972 | Klenke | 106/417 |
| 4,076,551 | 2/1978 | Bernhard et al. | 106/417 |
| 4,117,191 | 9/1978 | Kurrle | 428/330 |
| 4,626,472 | 12/1986 | Boutin | 428/407 |
| 4,710,375 | 12/1987 | Takasuka et al. | 424/69 |
| 4,772,331 | 9/1988 | Noguchi et al. | 106/417 |
| 4,956,019 | 9/1990 | Noguchi et al. | 106/415 |
| 4,985,187 | 1/1991 | Bes et al. | 264/13 |

FOREIGN PATENT DOCUMENTS

60-255712 12/1985 Japan.

*Primary Examiner*—George F. Lesmes
*Assistant Examiner*—Blaine R. Copenheaver
*Attorney, Agent, or Firm*—Millen, White, Zelano, & Branigan

[57] ABSTRACT

The application relates to deagglomerated and readily dispersible platelet-like substrates with a high degree of softness, which are characterized by a content of 0.5-20% by weight of spherical particles having a small diameter in comparison with the platelet-like substrate, and to a process for their preparation and their use.

16 Claims, No Drawings

PLATELET-LIKE SUBSTRATES

This application is a continuation of application Ser. No. 07/547,277, filed Jul. 3, 1990, now abandoned.

BACKGROUND OF THE INVENTION

The invention relates to deagglomerated and readily dispersible platelet-like substrates having a high degree of softness.

Platelet-like substrates, that is to say materials having a relatively low thickness in comparison with their length and width, are employed in many areas of industry. Thus, for example, platelet-like minerals, such as, for example, mica or talc, are employed in finely divided form as fillers for plastics. Platelet-like pigments, such as, for example, mica platelets coated with metal oxides or platelet-like iron oxide, are used both for pigmenting, for example, lacquers, paints, plastics and the like and in cosmetic formulations.

A fundamental problem is the marked tendency of such platelet-like substrates to form agglomerates in which the substrates lie on top of one another in a stack and because of strong adhesion can be separated again only with difficulty. This is all the more serious since high shearing forces must not be exerted during incorporation of platelet-like substrates into formulations because the thin substrates are easily destroyed.

Chemical coatings on the surface of such substrates have hitherto been proposed in particular for preventing agglomeration, which manifests itself both by non-uniform pigmenting of the formulations and, in the case of cosmetics, by an unpleasant feeling on the skin. Further, this can lead to an undesirable impairment of the optical properties, especially in case of platelet-like nacreous pigments. Nevertheless, in many cases even such methods are not successful, so that such substrates can be offered only in the form of suspensions and not in dry form.

SUMMARY OF THE INVENTION

It is therefore still an object of preventing agglomeration of platelet-like substrates handled in dry form and of providing readily dispersible substrates, if appropriate with a pleasant feeling on the skin.

It has now been found, surprisingly, that this object can be achieved by mixing the platelet-like substrate in dispersed form with essentially spherical particles, a deagglomerated flexible substrate powder being obtained after the suspension has been dried.

The invention thus relates to deagglomerated and readily dispersible platelet-like substrates with a high degree of softness, characterized by a content of at least 0.5% by weight of spherical particles having a small diameter in comparison with the platelet-like substrate.

The invention also relates to a process for the preparation of deagglomerated and readily dispersible platelet-like substrates of high softness, which is characterized in that a suspension of a platelet-like substrate is mixed with a suspension of spherical particles having a small diameter in comparison with the platelet-like substrate, and the substrate is isolated therefrom by filtering and drying.

The invention furthermore relates to the use of such substrates in industrial or cosmetic formulations.

Admixing of the spherical particles evidently prevents the platelet-like substrates from lying on top of one another to a noticeable extent and in this way from being able to exert strong adhesion. AS electron microscopy photographs show, the spherical particles attach themselves to the surface of the platelet-like substrate and therefore, like a type of ball bearing, enable the substrate platelets to be easily moved relative to one another.

In order to be able to have an optimum effect in this sense, the spherical particles should have a small diameter in comparison with the platelet-like substrate. Since platelet-like substrates having a maximum diameter of about 1–500 $\mu$m are particularly suitable, spherical materials having a diameter in the range from about 0.05 to 50 $\mu$m are preferred.

Particularly suitable spherical particles are inorganic materials, such as, for example, $SiO_2$, $TiO_2$ and $ZrO_2$. Spherical particles based on $SiO_2$ in a particle size range of about 3–15 $\mu$m are known, for example, as materials for high pressure liquid chromatography and are marketed, for example, as LiChrospher® by E. Merck, Darmstadt. Preferably, the substrate has a diameter of about 10–20 times greater than the diameter of the spherical particles.

However, even more finely divided materials are particularly preferably employed, especially materials having a particle size in the range from about 0.05 to 1 $\mu$m. Such particles are preferably employed in monodisperse form, that is to say with a particle size which is as uniform as possible. Such monodisperse spherical particles based on $SiO_2$, $TiO_2$ and $ZrO_2$ are known. Monodisperse $SiO_2$ can be prepared, for example, in accordance with DE-A1 -3,616,133, which is an equivalent to U.S. Pat. No. 4,775,520 but the corresponding materials also based on $TiO_2$ and $ZrO_2$ are also commercially available as dispersions. A commercial source for mono-disperse $TiO_2$ is the Istituto Guido Donegani, Novara, Italy.

The improved deagglomeration of the substrate particles can be observed sensorily in a very simple manner by the improved softness of the substrate powder felt when the dry substrate is brushed onto the skin. Surprisingly, it is found that significant improvements can already be achieved with very small amounts of the spherical materials. A significant improvement is thus already achieved with about 0.5% by weight. Outstanding results are already achieved when about 1.5–3% by weight of the spherical material is admixed. As a rule, amounts of about 0.5–20% by weight, preferably about 1–10% by weight, are therefore employed. Larger amounts can be mixed with the substrate without problems, but as a rule no further improvement in softness is achieved here.

As already mentioned, the dispersibility and softness of any desired platelet-like substrates can be improved with the addition according to the invention of spherical particles. As a rule, such substrates have a diameter of about 1–500 $\mu$m, in particular about 5–200 $\mu$m, and a thickness of abut 0.05–5 $\mu$m, in particular about 0.1–1 $\mu$m. Materials which may be mentioned in particular are: platelet-like zeolites, such as mica or talc, glass, platelet-like iron oxide, bismuth oxychloride, basic lead carbonate, barium sulfate, mica coated with metal oxide and metal flakes.

To prepare the mixtures according to the invention, a dispersion of the platelet-like substrate is mixed thoroughly with a dispersion of the spherical material and the mixture of solids is then isolated by filtration, if appropriate washing and subsequent drying. Washing and drying is appropriate when a dry product is desired.

Calcination may further be conducted without any loss of the pigment properties according to the invention.

It is of decisive importance here for the starting materials to be present in a well-dispersed form. For this, it may be advantageous for the admixing according to the invention of spherical particles to follow directly after the preparation of the particular platelet-like substrate as long as this is still in dispersed form.

Although perfectly spherical particles are preferred, nearly spherical particles are also operative in the invention.

However, a substrate which is already in the dry form and therefore already agglomerated can be very readily dispersed, for example, by stirring into a dispersing agent and by ultrasonic treatment. Such treatment is preferably carried out for a period of about 1–15 minutes, and preferably already in the presence of the spherical particles.

The nature of the dispersing agent is not critical per se. Water or a water-miscible solvent is preferably used, it also then depending from case to case on the dispersing agent in which the spherical particles are present. Commercially available monodisperse $SiO_2$, $TiO_2$ or $ZrO_2$ particles are often dispersed in ethylene glycol. However, other alcohols, such as, for example, glycerol, propanol or butanol, can be employed with an equally good effect.

The concentration of the platelet-like substrate and the spherical material in the dispersion is of only minor importance for achieving the effect according to the invention. The solids concentration is adjusted to within the range from about 1 to 50% by weight chiefly from economic considerations.

The platelet-like substrate can of course be mixed or coated with other substances in addition to being mixed with the spherical particles. Thus, for example, colored pigments can be admixed, or the substrate can be coated with colorless or colored metal oxides. The softness and the dispersing properties of the substrate are as a rule not adversely influenced by such further additives or treatment processes, all of which are known per se.

When the mixing operation has ended, the platelet-like substrate is separated off from the dispersion in the customary manner, for example by filtration, and if appropriate is also washed and dried and is then immediately ready for use. If appropriate, the pigment mixture can also be calcined without the effect suffering under this treatment.

The mixtures can be used widely both in industrial trial and in cosmetic formulations, such as, for example, printing inks, plastics mixtures, skin powder and the like.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosures of all applications, patents and publications, cited above and below, and of corresponding application(s) Federal Republic of Germany P 39 22 178, filed Jul. 6, 1989, are hereby incorporated by reference.

EXAMPLES

Example 1

50 ml of a 10% dispersion of Iriodin ® 504 (platelet-like pearl lustre pigment based on mica/$Fe_2O_3$ from E. Merck, Darmstadt) in ethylene glycol are treated with ultrasound for about 5-minutes, and 50 ml of a 10% dispersion of monodisperse $SiO_2$ having a particle size of about 300 nm are added in the course of 10 minutes, under further sound treatment. After a further 5 minutes of treatment with ultrasound, the product is filtered off and dried at 100° C. for 2 hours. A pigment with a very soft feeling on the skin is obtained.

Example 2

The procedure is analogous to Example 1, but Iriodin ® 225 (pearl lustre pigment from E. Merck, Darmstadt, based on mica/$TiO_2$) is employed as the platelet-like substrate and monodisperse $TiO_2$ ( P112F from Instituto Guido Donegani, Novara, Italy) is employed as the spherical particles.

Example 3

Iriodin ® 225 is reacted with monodisperse $SiO_2$ having a particle size of 200–250 run analogously to Example 1.

Example 4

200 ml of an aqueous suspension of 4.75 g of LiChrospher ® ( porous spherical silica gel having an average particle size of 5 μm) are added to a suspension of 10 g of Iriodin ® 100 (silver-coloured pearl lustre pigment based on mica/$TiO_2$ from E. Merck, Darmstadt) in 200 ml of water in the course of 50 minutes, the pH being kept at 8 with the aid of NaOH. After the mixture has been subsequently stirred for 2.5 hours, the solid is filtered off, washed and dried.

Example 5

Mica having a particle size of 1–50 μm is reacted with LiChrospher ® analogously to Example 4.

Example 6

290 ml of water, 3 drops of a surfactant and 0.33 g of gelatin are added to 210 ml of a suspension of monodisperse $SiO_2$ having a particle size of 475 nm and containing 2.35 g of $SiO_2$/100 ml in a water/ethanol/$NH_3$ mixture (32.2:64.2:3.6 parts by weight) and the mixture is stirred at room temperature for 15 minutes. After treatment with ultrasound for 30 minutes, the suspension is added to a suspension of 50 g of Iriodin ® 219 ( pearl lustre pigment based on mica/$TiO_2$ from E. Merck, Darmstadt) in 500 ml of water in the course of half an hour. The mixture is then brought to pH 6 with 10% aqueous hydrochloric acid, and a solution of 8.67 g of $CrCl_3.6H_2O$ in 500 ml of water is metered in over a period of 50 minutes, during which the pH is kept at 6.0 with 5% aqeuous sodium hydroxide solution. The product is then filtered off, washed chloride-free with water, dried and calcined at 900° C. Both the dried and the calcined pigment are distinguished by their high softness.

Example 7

The procedure is analogous to Example 6, but 7 g of $AlCl_3.6H_2O$ are employed instead of $CrCl_3.6H_2O$.

Example 8

A suspension of 5 g of Iriodin® 504 in 40.5 ml of ethylene glycol is treated with ultrasound for 5 minutes, and 25.2 ml of a suspension of monodisperse $SiO_2$ having a particle size of 475 nm in ethylene glycol ($SiO_2$ content: 12 g/l) are then added, while stirring. After renewed treatment with ultrasound, the product is separated off and dried at 110° C.

Example 9

A suspension of 5 g of Iriodin® 504 in 22.5 ml of glycerol and 22.5 ml of isopropanol is treated with 4.8 ml of monodisperse $SiO_2$ in glycerol (particle size 475 nm; $SiO_2$ content 62.5 g/l) analogously to Example 8.

Example 10

A suspension of 5 g of Iriodin® 504 in 45 g of n-butanol is treated with 9 ml of monodisperse $SiO_2$ in n-butanol (particle size 475 nm; $SiO_2$ content 33.3 g/l) analogously to Example 8.

Example 11

A suspension of 5 g of Iriodin® 504 in 45 ml of water is treated with 14.4 ml of monodisperse $SiO_2$ in water (particle size 475 nm; $SiO_2$ content 20.8 g/l) analogously to Example 8.

Example 12

The procedure is analogous to Example 11, but 5 g of Iriodin® 225 are employed.

Example 13

The procedure is analogous to Example 10, but 5 g of Iriodin® 225 are employed.

Example 14

The procedure is analogous to Example 9, but 5 g of Iriodin® 225 are employed.

Example 15

The procedure is analogous to Example 8, but 5 g of Iriodin® 225 are employed.

Example 16

100 g of mica having a particle size of about 10–50 μm are coated with $TiO_2$ by the process of DE-PS 2,009,566 using 250 ml of aqueous $TiCl_4$ solution (336 g of $TiCl_4$/l). After the suspension has been cooled to 30° C., 235.3 ml of a suspension of monodisperse $SiO_2$ (particle size 340–400 run; $SiO_2$ content 2.31 g/l) in a water/ethanol/$NH_3$ mixture (32.2:64.2:3.6 parts by weight) are added at a pH of 4.0 in the course of one hour, the mixture is subsequently stirred for a further 15 minutes and the product is separated off, washed chloride-free with water, dried and calcined at 800° C. for 30 minutes.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A deagglomerated, readily dispersible platelet-shaped material comprising platelet-shaped substrates and coated thereon an amount of spherical particles sufficient to render the substrate readily dispersible and deagglomerated, wherein said platelet-shaped substrates have a maximum diameter of about 1 to about 500 μm and said spherical particles have a diameter from about 0.05 to about 50 μm and wherein the spherical particles exert a ball-bearing effect on the platelet-shaped substrates enabling the platelet-shaped substrates to move relative to one another.

2. A material of claim 1, comprising at least 0.5% by weight, based on the substrate, of spherical particles.

3. A material of claim 1, wherein the spherical particles are monodisperse $SiO_2$ or $TiO_2$.

4. A material of claim 3, wherein the spherical particles have a diameter of about 0.05 to 1.0 μm.

5. A material of claim 1, wherein the platelet-like substrate is a zeolite, glass, iron oxide, bismuth oxychloride, lead carbonate, barium sulfate or metal flakes.

6. A material of claim 1, wherein the substrate is mica, talc or mica coated with metal oxides.

7. A material of claim 1, wherein the platelet-shaped substrate is an inorganic material.

8. A material of claim 1, wherein the spherical particles are inorganic materials.

9. A material of claim 1, wherein the spherical particles are $SiO_2$, $TiO_2$, or $ZrO_2$.

10. A material of claim 1, wherein the substrate is additionally coated with a colorless or colored metal oxide or an oxide hydrate thereof.

11. A material of claim 1, wherein the substrate is additionally coated with chromium oxide or aluminum oxide or an oxide hydrate thereof.

12. A material of claim 1, further comprising a surfactant, gelatin or gel.

13. A process for the preparation of the material of claim 1, comprising mixing a suspension of a platelet-shaped substrate with a suspension of spherical particles having a small diameter in comparison with the platelet-shaped substrate, wherein both suspensions are acidic and optionally one or both contain surfactants, gelatin or a gel, and optionally the material is coated with metal oxide or an oxide hydrate thereof, isolating the material from the suspension by filtering, drying the material, and optionally subjecting it to calcination.

14. In an industrial formulation containing a platelet-shaped material, the improvement wherein said platelet-shaped material comprises a deagglomerated, readily dispersible platelet-shaped material comprising platelet-shaped substrates and coated thereon, an amount of spherical particles sufficient to render the substrate readily dispersible and deagglomerated, wherein said platelet-shaped substrates have a maximum diameter of about 1 to about 500 μm and said spherical particles have a diameter from about 0.05 to about 50 μm and wherein the spherical particles exert a ball-bearing effect on the platelet-shaped substrates enabling the platelet-shaped substrates to move relative to one another.

15. A material of claim 9, wherein the spherical particle is $SiO_2$.

16. In a cosmetic preparation containing a platelet-shaped material, the improvement wherein said material comprises a deagglomerated, readily dispersible platelet-shaped material comprising platelet-shaped substrates and coated thereon, an amount of spherical particles sufficient to render the substrate readily dispersible and deagglomerated, wherein said platelet-shaped substrates have a maximum diameter of about 1 to about 500 μm and said spherical particles have a diameter from about 0.05 to about 50 μm and wherein the spherical particles exert a ball-bearing effect on the platelet-shaped substrates enabling the platelet-shaped substrates to move relative to one another.

* * * * *